(12) United States Patent
Visinoni

(10) Patent No.: US 7,075,045 B2
(45) Date of Patent: Jul. 11, 2006

(54) AUTOMATIC, MICROWAVE ASSISTED TISSUE HISTOPROCESSOR

(75) Inventor: Franco Visinoni, Sorisole (IT)

(73) Assignee: Milestone S.r.l., Sorisole (IT)

( * ) Notice: Subject to any disclaimer, the term of this patent is extended or adjusted under 35 U.S.C. 154(b) by 28 days.

(21) Appl. No.: 11/066,577

(22) Filed: Feb. 25, 2005

(65) Prior Publication Data

US 2005/0269315 A1    Dec. 8, 2005

(30) Foreign Application Priority Data

Jun. 7, 2004    (EP) .................................. 04013367

(51) Int. Cl.
*H05B 6/64* (2006.01)

(52) U.S. Cl. .................................. 219/685

(58) Field of Classification Search ................ 219/685, 219/680, 628; 118/50; 427/2; 436/180; 435/173.4, 40.1; 264/109, 239
See application file for complete search history.

(56) References Cited

U.S. PATENT DOCUMENTS

| | | | |
|---|---|---|---|
| 4,141,312 A | 2/1979 | Louder et al. ................ 118/7 |
| 4,656,047 A | 4/1987 | Kok et al. ..................... 427/2 |
| 5,023,187 A * | 6/1991 | Koebler et al. .............. 436/180 |
| 6,207,408 B1 | 3/2001 | Essenfeld et al. ........... 435/40.5 |
| 6,404,906 B1 * | 6/2002 | Bacus et al. ................ 382/128 |
| 6,586,713 B1 * | 7/2003 | Essenfeld et al. ........... 219/679 |
| 6,615,763 B1 * | 9/2003 | Edwards ...................... 118/46 |
| 6,674,884 B1 * | 1/2004 | Bacus et al. ................ 382/133 |
| 6,681,035 B1 * | 1/2004 | Bamford et al. ............ 382/133 |
| 6,797,928 B1 * | 9/2004 | Giberson et al. ........... 219/679 |
| 6,930,292 B1 * | 8/2005 | Winther et al. ............. 219/635 |
| 6,951,663 B1 * | 10/2005 | Edwards .................... 427/2.11 |
| 2001/0051365 A1 | 12/2001 | Morales et al. ........... 435/173.4 |
| 2002/0177183 A1 | 11/2002 | Giberson et al. ........... 435/40.5 |

FOREIGN PATENT DOCUMENTS

| | | |
|---|---|---|
| DE | 44 00 815 A1 | 7/1995 |
| EP | 822 403 B1 | 2/1998 |
| WO | WO 98/05938 | 2/1998 |

OTHER PUBLICATIONS

"The Two-Step Vacuum-Microwave Method for Histoprocessing", Boon et al., Microwave Newsletter, 1995, pp. 349-358.

European Search Report in 04013367.0-2209 dated Sep. 14, 2004.

"The Two-Step Vacuum-Microwave Method for Histoprocessing", Boon et al., European Journal of Morphology, vol. 33, No. 4, 1995, pp. 349-358.

\* cited by examiner

*Primary Examiner*—Daniel Robinson
(74) *Attorney, Agent, or Firm*—Marshall, Gerstein & Borun LLP

(57) ABSTRACT

A system and for automatic histoprocessing of organic tissue specimens using microwaves, two cavities and automatic fluid and specimen transfer between the two cavities.

30 Claims, 2 Drawing Sheets

AUTOMATIC, MICROWAVE ASSISTED TISSUE HISTOPROCESSOR

The present invention relates to the processing organic tissues to prepare them for further investigation. More specifically the present invention relates to the processing of organic tissues via a combination of microwave, vacuum treatments comprising the steps of fixing an organic sample, dehydrating and clearing the sample and subsequently infiltrating and embedding the sample in a supporting medium. The organic sample is thus prepared e.g. for basic Haematoxylin and Eosinstains and further techniques such as histochemical staining, IHC staining, decalcification, in-situ hybridisation etc., for subsequent examination by light and/or electron microscopy.

Specimens for diagnostic pathology and for anatomy pathology are presently prepared according to a conventional method, which is based on the following essential steps:

The tissue to be examined is treated with formalin or a saline solution to stop the process of decay and to stabilize the tissue so as to protect it against the physical and chemical rigours of processing.

In the second step the sample is dehydrated, i.e. some or all of the free water contained in the specimen is removed therefrom. During this procedure various cellular components are dissolved by the dehydrating fluids, such as lipids, which are extracted, and water soluble proteins, which are dissolved in aqueous alcohols.

The third step includes the treatment of the tissue with another solvent, the so-called clearing agent (which also removes lipids). Clearing is the transition step between dehydration and infiltration with a supporting medium. Since many dehydrants are immiscible with said subsequently applied supporting medium, a solvent is used which is miscible both with the dehydrant and the embedding medium to facilitate the transition between dehydration and infiltration steps.

The last step in the processing of organic specimens involves infiltrating the tissue cavities and cells by the supporting medium and finally embedding the tissue in the medium which will provide sufficient external support during the ensuing processing.

These known procedures show, however, a variety of disadvantages, such as a long processing time of the specimens which may amount up to 50 hours per sample. Furthermore, a huge amount of the dehydrating agent and the clearing agent has to be employed. In a normal procedure the specimens are treated several times with the dehydrating agent, e.g. ethanol in rising concentrations (up to 100% ethanol), and subsequently several times with the clearing agent in order to get rid of the dehydrating agent. Since large amounts of solvents have to be used, said solvents even being of high purity, the costs of such procedures are considerable.

A histoprocessing procedure with a shortened processing time is known from the article 'The Two-Step Vacuum-Microwave Method for Histoprocessing' by M. E. Boon et al., European Journal of Morphology, Vol. 33, No. 4, 1995, pages 349–358. The histoprocessing method of organic tissues disclosed therein includes the steps of fixing the tissue, dehydrating the sample, clearing the sample and embedding the sample in paraffin, whereby the dehydrating and the clearing of the sample are carried out simultaneously in 100%-isopropanol in a vacuum chamber and heated by microwaves. Isopropanol is used in this step because it is both a weak dehydrator and a clearing agent. In this step the temperature is controlled at 55° C. and the pressure at 0.04 Mpa (400 mbar) such that the tissue can withstand the hazards of the treatment without adverse affects.

EP 0 822 403 B1 "Process for processing organic specimens" teaches to carry out dehydration and the clearing step simultaneously by applying a mixture of a dehydration agent and an essentially lipophilic agent.

U.S. Pat. No. 6,207,408 B1 discloses a high quality, continous throughput, tissue fixation-dehydration-fat removal-impregnation method.

In view of said prior art it is the object of the present invention to propose a technique to further reduce the time necessary for processing organic tissue e.g. for diagnostic pathology purposes.

Said object is achieved by means of the features of the independent claims. The dependent claims develop further the central idea of the present invention.

According to a first aspect of the present invention, a system for processing tissue samples is proposed. The system comprises at least a first and a second cavity into which tissue samples can be inserted. A fluid transfer system is provided for selectively transferring one or more fluids from respective storage containers in and out of the first cavity. A microwave heating device is provided to apply a microwave radiation to the inside of the first cavity. Furthermore, a device for automatically transferring tissue samples from the first cavity to the second cavity is proposed.

Thereby, the second cavity can be operatively connected to at least one heating, such as f.e. a resistive heating.

Optionally a dedicated system applies vacuum to the first and/or the second cavity.

The automatic transfer device for the tissue samples can be a robotic arm having two or more degrees of freedom.

According to a further aspect of the present invention, a microwave chamber is proposed having an opening for inserting a sample holder, the sample holder being operatively connected to a cover sealing the opening of the microwave chamber upon insertion of the sample holder. The microwave chamber furthermore presents at least one opening for directly filling the interior of the microwave chamber at least partially with a fluid as well as for subsequent evacuation (draining) of the fluid out of the microwave chamber.

The cover of the sample holder can seal the microwave chamber to prevent microwave leakage.

The sample holder can for example hold one or more juxtaposed layers of organic specimen holders (cassettes).

Both cavities of the system can be optionally equipped with a programmable stirring motor activating, through magnets, a stirring bar placed at the bottom of the cavity. The movement of the stirring bar assures a homogeneous mixing of the solution and therefore temperature homogeneity.

Both cavities of the system can be optionally equipped with suitable temperature measurement and control systems to enable the user to program different temperature ramping times and time-at-temperature periods according to the requested procedure.

At least one sensor can be provided for detecting the fluid level inside the microwave chamber.

According to a still further aspect of the present invention, a method for processing organic tissue samples for pathology purposes is proposed. The tissue samples to be processed are inserted in a microwave chamber. Without removing the tissue samples to be processed, sequentially one or more (f.e. different) fluids for processing the tissues samples are pumped in and out of the microwave chamber. Microwave power can be applied to the microwave chamber during the presence of at least one of the fluids in the microwave chamber in order to increase the temperature of the fluid present in the microwave chamber. E.g. during the evaporation step, microwave power can also be applied to the first cavity without a fluid being present.

The pressure in the microwave chamber can be reduced, i.e. a vacuum can be applied either with or without microwave irradiation.

The fluid reagents can be pumped from storage containers into the microwave chamber by applying a vacuum to the microwave chamber.

The fluid reagents can be pumped from the microwave chamber back to storage containers by applying a vacuum to the storage containers.

A fluid reagent can be transferred, via the microwave chamber, from a refilling storage container (tank) to corresponding operating tanks. To this purpose a vacuum is applied to the microwave chamber in order to suck in the reagent from the refilling storage tanks to the microwave chamber.

The purpose of passing fluids first to the microwave chamber is to be able to measure the amount of fluid (through a level sensor) being loaded to the corresponding operating tank.

Subsequently, the reagent can be drained from the microwave chamber to the corresponding operating tank, for example passively via gravity force or actively by pumping means or means for applying a vacuum.

When the reagents in the operating tanks are exhausted, the reverse procedure can be utilized to transfer them to the exhaust tank.

In a following step the samples can be automatically transferred into a second cavity in which they are processed with an impregnation medium such as e.g. heated wax etc. in order to impregnate the sample.

During the processing of the samples with the impregnation medium (for example heated wax), vacuum can be applied to the second cavity in order to promote the impregnation process.

In the microwave chamber at least one of the steps of fixation, alcohol rinsing, dehydration, clearing or simultaneous dehydration/clearing and vacuum drying of the organic specimen can be carried out.

The method can furthermore comprise the steps of magnetically stirring the liquid reagents in the microwave chamber and the resistance heated impregnation chamber to assure temperature homogenization of fluids.

According to a further aspect of the present invention, the use of a method as set forth above is proposed for processing organic samples, both of human or animal origin, but not limited to (e.g. plant tissue) etc.

Further features, advantages and objects of the present invention will became evident for the person skilled in the art when reading the following detailed explanation of an embodiment of the present invention taken in conjunction with the figures of the enclosed drawings.

Figure 1:
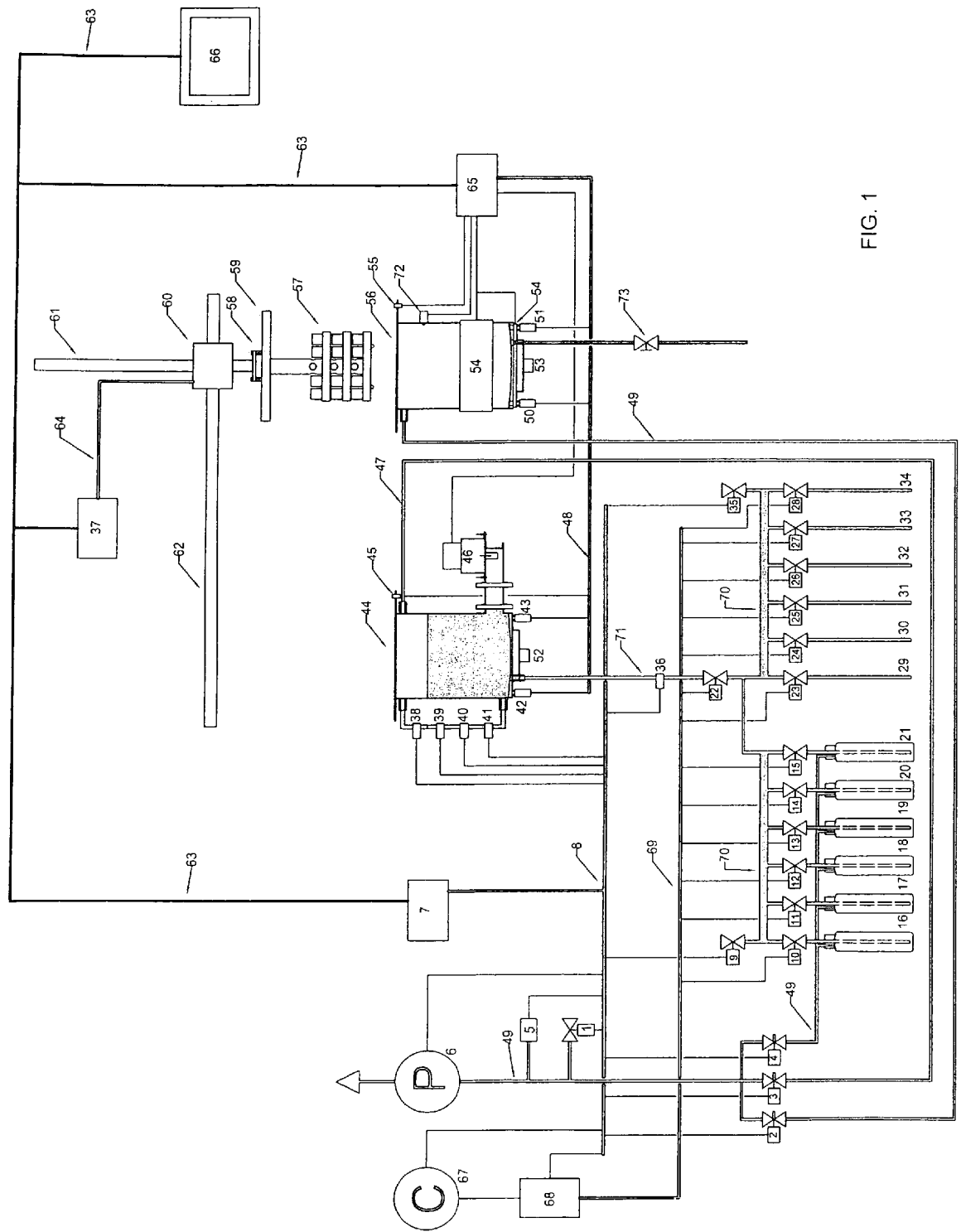
FIG. 1 shows a schematic drawing of a tissue processing system which can be used with connection to the present invention. The figure shows a fully automated organic tissue processor which enables reduction of the time necessary for preparing organic tissues for diagnostic purposes.

As shown in the figure, the system comprises a first microwave cavity 44 for example made from stainless steel. Furthermore, the system comprises a separate second cavity 56, which, in contrast to the first cavity 44 heated by coupling microwave radiation from a magnetron 46, is heated via one or more resistive heating element 54 functionally connected f.e. to the wall and/or bottom of the second cavity 56. Note that the second cavity can comprise several heating elements provided respectively at different positions at the second cavity and optionally being of different nature.

The microwave cavity 44 can be used for several sequential steps of the tissue preparation process as defined in the introductory portion of the specification.

In order to carry out several different steps of the tissue preparation process sequentially within the same microwave cavity 44, said cavity 44 is designed such that one or more, especially different fluids from containers 16, 17, 18, 19, 20 and 21 can be selectively transferred into and drained from the microwave cavity 44.

Note that usually fluids from different storage containers are used sequentially, however, in some case also a mixture of fluids of different storage containers can be used.

This process as well as other processes is controlled via an electronic board 7. For the pumping and draining process of the microwave cavity 44 the electronic board 7 controls pneumatic valves 10, 11, 12, 13, 14, 15 (respectively one for each of the containers 16, 17, 18, 19, 20, 21) and a vacuum pump 6 for applying a vacuum to the interior of the microwave cavity 44 in older to suck in the selected fluid from any or several of the containers 16 to 21.

Before carrying out the corresponding histoprocessing step, at first a fluid from any of the containers 16 to 21 is transferred into the microwave cavity 44. Then one of the sample preparation steps is carried out under application of microwave power from the magnetron 46 (if needed), and subsequently the fluid used for the specific step is drained from the microwave cavity 44 either passively via gravity force or actively with vacuum into the containers, The used fluid from the microwave cavity 44 is thus drained back to the respective container 16 to 21 from which it has been initially sucked into the microwave cavity 44. Usually a fluid can be used for several cycles of the histoprocessing sequence.

The organic samples to be processed are held in a PTFE rack 57 having for example 210 specimens holders (cassettes), respectively one for each sample. The rack 57. is functionally connected to a metal cover 59 for the microwave cavity 44. When the rack 57 is inserted into the microwave cavity 44, the cover 59 will close the microwave cavity 44 in a microwave-leak-proof fashion when the rack 57 is entirely inserted into the cavity 44. Note that the rack, when entirely inserted, has some clearance to the bottom wall of the microwave cavity.

Note that according to the present invention the transfer of the rack 57 attached to the cover 59 in and out of the microwave cavity 44 (as well as a transfer to at least a second cavity 56 as will be explained later on) is carried out by an automated device, which according to the present example is a robot device having at least two degrees of freedom (X- and Y-axis). Note that the automated device can also be designed for other or additional movements such as e.g. rotational degrees-of-freedom.

The robotic device 60 according to the present example has a vertical robotic arm 61 as well as a horizontal arm, 62 along which the rack 57 and the cover 59 can be moved horizontally and vertically in FIG. 1.

Note that the robotic device 60 is controlled by a dedicated electronic board 37 controlling the robotic arm movement and thus the sample holder transfer.

Once all necessary tissue processing steps using a certain fluid have been performed, the fluid is pumped out. Prior to the transfer to the wax impregnation in the second cavity the samples are usually subjected to vacuum drying in the microwave cavity 44, in the absence of fluid to remove superficial fluids from the tissue surface and part thereof from within the samples. This vacuum drying step may be performed with or without microwaves. The specimen held in the racks 57 can then be transferred into a second cavity 56 made e.g. of stainless steel or any other suited material, to complete the tissue processing for example via the impregnating step using paraffin wax.

To this regard, the robotic device 60 is controlled by the electronic board 37 to first move the rack 57 vertically out of the cavity 44, then to horizontally transferred to a position over the second cavity 56 and finally, to insert it vertically into the second cavity 56. Again, the cover 59 will close the second cavity 56.

Note that in contrast to the first cavity there is no need for a fluid transfer functionality of the second cavity. Usually the impregnation medium is always present in the second cavity, i.e. during repeated cycles of the histoprocessing procedure and will be replaced from time to time. In any case there is no exchange of fluids in the second cavity during histoprocessing procedure.

Usually, said impregnation medium is a wax which is liquid when heated to the melting point temperature or above via the one or more heating elements 54.

In order to promote and accelerate the impregnation step, a vacuum can be applied to the second cavity 56 via the vacuum pump 6.

As soon as the impregnation step is finalized in the second cavity 56, the samples held in the rack 57 are moved outside by the robotic device 60 and can then be used for further investigation procedures.

Note that the sample rack 57 as shown in the embodiment can comprise several layers of juxtaposed specimen cassettes (in the present embodiment three juxtaposed layers of sample cassettes).

The minimum number of necessary cavities for carrying out all necessary sample processing steps therefore, according to the present invention can be reduced to two as apart from the impregnation step all other previous sample processing steps can be carried out within the same microwave cavity 44.

Time can be saved by the fact that while different subsequent processing steps are carried out in the same cavity 44, the samples can remain in said cavity 44 and no intermediate transfer etc. is necessary. While the samples remain within the cavity 44, the necessary fluids from the storage container 16 to 21 are sucked in and drained, respectively. Time is also saved, compared to conventional heated histoprocessing systems, by application of microwave irradiation.

It is important to note that although the first cavity 44 is functionally connected to a magnetron 46, it is not necessary to apply microwave power during all the processing steps carried out in the first cavity.

Note that also the pressure in the microwave chamber can be reduced by using the vacuum pump 6 during any of the tissue processing steps carried out in the first cavity 44.

Typical steps carried out in the first cavity 44 are the steps of fixation, alcohol rinsing, dehydration, clearing and/or vacuum evaporation of the samples.

The embodiment shown in FIG. 1 is provided with a substantial number of additional safety and sensor devices which shall be explained in the following.

References 51/50 designate temperature sensors such as for example a PT100 temperature sensor for detecting the temperature within the second (wax) cavity 56 and being placed either at the bottom or laterally at the wall of the cavity 56.

References 52 and 53 respectively designate stirring devices for the first and second cavity which can be activated magnetically. The rotation of the stirring devices is electronically controlled by a dedicated electronic board.

Reference 55 designates a microswitch which is a safety device for ensuring a proper closing of the top of the second cavity 56.

The reference 58 designates a spring loaded connections between the robotic device 60 and the sample holder in order to keep the cover 59 under a spring loaded pressure when it is closing the first cavity 44 or the second cavity 56.

Reference 63 designates a communication cable in order to connect the several electronic boards 7, 37 and 65 as well as a user interface 66 which can be a touch screen terminal.

Reference 64 designates the wiring to connect the electronic board 37 with all connected sensors and devices.

Reference 65 designates an electronic board which is specifically designated to operate and control the heating of the first and second cavity.

Reference 68 designates an electro/pneumatic valve group which is used to distribute compressed air from the compressor 67 (having an air container and being controlled by the electronic board 7) to pneumatic valves 22 to 28 and 10 to 15.

Reference 69 designates pneumatic connection, i.e. the pneumatic tubing between the pneumatic valve group 68 and the controlled pneumatic valves 10 to 15, 23 to 28.

Reference 1 designates a proportional valve for modulating the vacuum for example applied to the cavities 44 and 56 and/or to any of the storage containers 16 to 21. Valve 1 is controlled by the micro controllers installed on the electronic board 7.

Reference 2 designates an electric valve controlling the communication of the vacuum pump 6 and the second cavity 56, wherein said electric valve is controlled by the micro controller installed on the electronic board 7.

Correspondingly, reference sign 3 designates an electronic valve for the communication between the vacuum pump 6 and the first (microwave) cavity 44, which electric valve 3 is also controlled by the micro controller installed on the electronic board 7.

Finally, reference 4 designates an electric valve for the communication between the vacuum pump 6 and the in-used reagent storage containers 16 to 21.

Reference 5 designates a pressure sensor for the absolute pressure in the vacuum circuitry. The output value of the pressure sensor 5 is supplied to the electronic control board 7 to control the vacuum in the vacuum circuitry.

Reference sign 8 designates a circuitry for the communication between the electronic board 7 and the connected sensors, valves and devices.

Reference 9 designates an electric valve to allow air from the atmosphere (fresh air) to get into the manifolds 70.

References 10 to 15 designate pneumatic valves for opening respectively one of the associated storage container 16 to 21.

Reference 22 designates a pneumatic valve for the communication between the manifolds 70 and first cavity 44.

References 23 to 28 designate a pneumatic valves respectively opening and closing tubes for loading new fluid reagents and unloading exhausted fluid reagents 29 to 34.

Reference 35 designates an electric valve corresponding to the electric valve 9.

Reference 36 designates a level sensor checking the presence and the level of a fluid reagent in the loading tube.

References 38 to 41 are level sensors respectively responding to difference levels of fluid reagents in the first (microwave) cavity 44.

References 42 and 43 are temperature sensors for reading the cavity temperature of the first microwave cavity 44 at different positions and being placed either at bottom or laterally at the wall of cavity 44.

Reference 45 designates at least one but preferably at least three safety switches detecting a proper (microwave sealed) closure of the opening of the cavity 44 by the cover 59.

Reference 47 designates a tube connecting the microwave cavity 44 with the vacuum pump 6 in order to lower the pressure within the cavity 44 which can be used, for example to suck in fluid reagents from the storage container 16 to 21, 29 to 34 and/or to reduce the pressure during the application, but not limited to, of microwave power to any samples and fluids being present within the cavity 44.

Reference 48 designates the wiring through which the electronic board 65 communicates with the connected sensors and devices.

Finally, reference 49 designates a tube connecting the second cavity (for impregnation) 56 with the vacuum pump 6 in order to reduce the pressure within the second cavity and thus to promote and accelerate the impregnation process.

Reference 72 is a level sensor for verifying the presence and the level of the liquid state of the wax for the second cavity 56.

Figure 2:
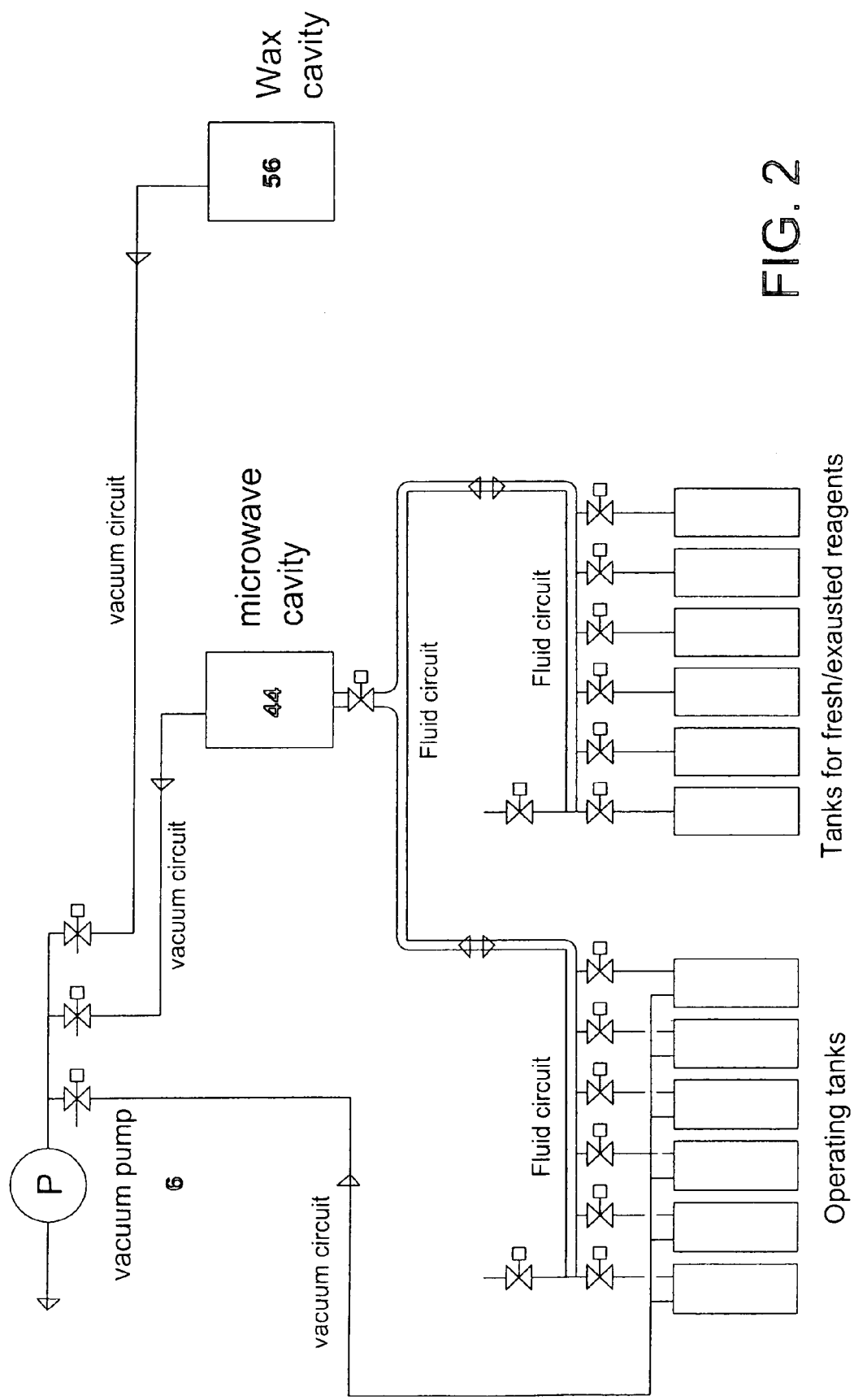
FIG. 2 shows schematically the fluid transfer functionality of a system according to the present invention.

FIG. 2 shows schematically that the vacuum pump 6 is operationally connected both to the first cavity 44 and the second cavity 56. According to this example, by applying a vacuum to the microwave cavity 44 liquids from the storage containers can be sucked into the microwave cavity. Once the presence of a specific liquid is no longer needed in the cavity 44, the respective liquid can be drained out of the cavity 44 and back to the operating tank by opening a valve at the bottom of the first cavity 44 such that the liquid will flow back to the operating tank due to the gravity force or vacuum in the operating tank.

In the present embodiment a vacuum is applied to the second (impregnation or wax) cavity 56. However, in this embodiment no automatic draining functionality is provided for the second cavity 56. A manual draining reference 73 is positioned below the cavity 56.

The main advantages of the present invention can be described as follows:

The system according to the present invention applies microwave radiation to a microwave cavity which also serves as a processing chamber into which cassettes for holding the organic specimen can be placed and fluid reagents can pumped in and out.

The microwave processing can be automated by applying microwave radiation to reagents that are sequentially pumped in and out of the (single) microwave chamber.

The system has two processing chambers for processing the tissues, wherein one can be exclusively for microwave radiation enhanced processing and one second the for the impregnation step. The design of the invention presented is not limited to two cavities (microwave and non-microwave). E.g. a second duplicate set of the described chambers above can also be set up allowing the ability for parallel histoprocessing (twin processing). This allows for a greater number of samples to be prepared rapidly simultaneously. Furthermore, more than two cavities can be used sequentially.

The impregnation for example by wax can be achieved by transferring the cassettes from the microwave chamber to a separate, single chamber in which melted paraffin wax is present.

Vacuum can be applied for partial drying in the first, (microwave) cavity, and

The wax impregnation can be performed at reduced pressures of within the range 50–900 mBar, for example 100 mbar.

The cassette rack can hold up to e.g. 210 cassettes (three layers of 70 cassettes), Up to six different microwave steps can be carried out, Tissue samples up to 5 mm ore more can be processed.

A magnetic agitation (stirring) can be carried out for all steps with the exception of the vacuum drying step. The rotational speed of the stirrer can be controlled automatically, The first cavity is used for all steps with the exception of the impregnation step, i.e. the fixation, alcohol rinsing, dehydration and clearing including the vacuum drying.

The fluid reagent management can be achieved by emptying the selected storage container below the working bench by pumping the used reagents into the microwave chamber and then pumping it to a waste container placed in a loading position adjacent to the main reagent storage containers. A reversed process can then be carried out by substituting the waste container with a fresh fluid container, which "fresh" reagent can then be pumped back into the main storage container via the microwave chamber. This process can sequentially be repeated for each reagent that requires replacement.

A preferred method of histoprocessing human and animal, but not limited to, tissues with thickness up to 5 mm but not limited to, comprises the following steps:

1. First step: Fixation of tissue with either formalin or formalin substitute (preferably ethanol based for improved protein, DNA, RNA recovery) at temperature above physiological (37° C.) under microwave irradiation and magnetic stirring of reagents for temperature homogeneity in the cavity.
2. Second step: Rinsing with alcohol, preferably ethanol, at ambient temperature under normal pressure.
3. Third step: Dehydration of tissues with either ethanol, but not limited to, or mixtures of two or more alcohols at temperature above physiological (37° C.) under microwave irradiation and magnetic stirring of reagents for temperature homogeneity in the cavity.
4. Fourth step: Clearing (removing lipids) with isopropanol under microwave irradiation and magnetic stirring of the reagents for temperature homogeneity in the cavity.

4a. In alternative example, simultaneous dehydration/clearing under microwave irradiation and stirring of reagents for temperature homogeneity with a mixture of ethanol plus isopropanol plus a long-chain hydrocarbon for applications with fatty or very fatty tissues as a single step substituting steps 3 and 4.

4b. As a further alternative example, simultaneous dehydration/clearing with a mixture of ethanol plus isopropanol under microwave irradiation and magnetic stirring for temperature homogeneity for low fat or non fatty tissues substituting steps 3 and 4.

5. Fifth Step: Evaporation of the tissues under process without the presence of any reagents under programmable vacuum condition in the range of 50–900 mbar to eliminate excess amount of reagents both superficially and from within the tissue avoiding complete drying of specimen. This step shortens the subsequent wax impregnation time and eliminates contamination of wax. The step is carried out with or without low microwave irradiation to speed up the process.

6. Sixth step: Wax impregnation of tissues under programmable (increasing steps) of vacuum in the range 50–900 mbar under magnetic stirring for temperature homogeneity with a single type wax. This step under vacuum eliminates residual traces of reagents improving wax, infiltration of tissue and simultaneously "cleaning" the wax for further use.

(Prior to samples being transferred from the microwave chamber to the wax impregnation chamber, samples are treated with vacuum in the absence of fluid, with or without microwave power. This process is to remove excess fluid from the tissue).

The invention claimed is:

1. A system for automatic histoprocessing of organic tissues specimens, comprising:
   at least a first cavity and a second cavity in which tissue specimens can be processed,
   a system to selectively transfer at least one fluid reagent from a storage container in and out of the first cavity, and
   a device for automatically transferring said tissue specimens from the first cavity to the second cavity.

2. A system according to claim 1, comprising a microwave generating device for applying microwave radiation to the inside of the first cavity, the first cavity being connected to the microwave generating unit.

3. A system according to claim 1, comprising at least one resistive heating element to which the second cavity is functionally connected.

4. A system according to claim 1, comprising means for applying a vacuum to at least one of the first cavity and the second cavity.

5. A system according to claim 1, wherein the automatic transfer device is a robot device.

6. System according to claim 5, wherein the robot device is a robot arm having at least two degrees-of-freedom.

7. A method for processing tissue samples, the method comprising the following steps:
   inserting tissue samples to be processed into a microwave chamber, and
   without removing the tissue samples to be processed from the microwave chamber, sequentially pumping in and out of the microwave chamber at least two fluid reagents for processing the tissue samples, wherein microwave power is applied to the microwave chamber during the presence of at least one of the reagents in them microwave chamber in order to increase the temperature of the reagent present.

8. A method of histoprocessing tissues, comprising the following steps:
   First step: fixing tissue with either formalin or formalin substitute under microwave irradiation and magnetic stirring of said reagents,
   Second step: rinsing the tissue with alcohol at ambient temperature under normal pressure,
   Third step: dehydrating the tissue with one alcohol or a mixture of different alcohols under microwave irradiation and magnetic stirring,
   Fourth step: clearing under microwave irradiation and magnetic stirring of the reagents,
   Fifth step: evaporating the tissue under process without the presence of any reagents under programmable vacuum condition to eliminate excess amount of reagents both superficially and from within the tissue while avoiding complete drying of specimen,
   Sixth step: impregnating the tissue with wax under programmable vacuum and under magnetic stirring.

9. A method according to claim 8, comprising carrying out the third step and the fourth step by a simultaneous dehydration/clearing under microwave irradiation and stirring of reagents for temperature homogeneity with a mixture of ethanol plus isopropanol plus a long-chain hydrocarbon for applications with fatty or very fatty tissues.

10. A method according to claim 8, comprising carrying out the third step and the fourth step by a simultaneous dehydration/clearing with a mixture of ethanol plus isopropanol under microwave irradiation and magnetic stirring for temperature homogeneity for low fat or non fatty tissues.

11. A method according to claim 7, comprising reducing the pressure in the microwave chamber during the application of the microwave power in the evaporation stage.

12. A method according to claim 7, comprising pumping the fluid reagents from storage containers into the microwave chamber by applying a vacuum to the microwave chamber.

13. A method according to claim 7, comprising pumping the fluid reagents from the microwave chamber to storage containers by applying a vacuum to the storage containers.

14. A method according to claim 13, comprising transferring a fluid reagent from a first storage container to a second storage container by
   applying a vacuum to the microwave chamber in order to pump the reagent from the first storage container to the microwave chamber, and
   draining the reagent from the microwave chamber to the second storage container.

15. A method according to claim 7, comprising the further step of automatically transferring the specimen into a second cavity in which they are processed with an impregnation medium.

16. A method according to claim 15, comprising applying a vacuum to the second cavity during the processing of the sample with the impregnation medium.

17. A method according to claim 16, comprising applying the vacuum in increments.

18. A method according to claim 11, comprising carrying out at least one of the steps of fixation, alcohol rinsing, dehydration, clearing and vacuum drying out the specimens in the microwave chamber.

19. A method according to claim 7, comprising the step of magnetically stirring the fluid reagent in the microwave chamber during application of the microwave radiation and/or during the impregnation process in the second chamber.

20. A method according to claim 7, comprising histoprocessing organic pathological samples.

21. A method according to claim 12, comprising reducing the pressure in the microwave chamber during the application of the microwave power in the evaporation stage.

22. A method according to claim 8, comprising pumping the fluid reagents from storage containers into the microwave chamber by applying a vacuum to the microwave chamber.

23. A method according to claim 8, comprising pumping the fluid reagents from the microwave chamber to storage containers by applying a vacuum to the storage containers.

24. A method according to claim 8, comprising transferring a fluid reagent from a first storage container to a second storage container by applying a vacuum to the microwave chamber in order to pump the reagent from the first storage container to the microwave chamber, and draining the reagent from the microwave chamber to the second storage container.

25. A method according to claim 8, comprising the further step of automatically transferring the specimen into a second cavity in which they are processed with an impregnation medium.

26. A method according to claim 25, comprising applying a vacuum to the second cavity during the processing of the sample with the impregnation medium.

27. A method according to claim 26, comprising applying the vacuum in increments.

28. A method according to claim 8, comprising carrying out at least one of the steps of fixation, alcohol rinsing, dehydration, clearing and vacuum drying out the specimens in the microwave chamber.

29. A method according to claim 8, comprising the step of magnetically stirring the fluid reagent in the microwave chamber during application of the microwave radiation and/or during the impregnation process in the second chamber.

30. A method according to claim 8, comprising histoprocessing organic pathological samples.

* * * * *